(12) United States Patent
Nishtala et al.

(10) Patent No.: US 8,328,792 B2
(45) Date of Patent: Dec. 11, 2012

(54) ENHANCED PRE-WETTED INTERMITTENT CATHETER WITH LUBRICIOUS COATING

(75) Inventors: Vasu Nishtala, Snellville, GA (US); Michael O'Grady, Monroe, GA (US); Robert Young, Loganville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 591 days.

(21) Appl. No.: 12/091,916

(22) PCT Filed: Oct. 25, 2006

(86) PCT No.: PCT/US2006/041633
§ 371 (c)(1),
(2), (4) Date: Feb. 2, 2009

(87) PCT Pub. No.: WO2007/050685
PCT Pub. Date: May 3, 2007

(65) Prior Publication Data
US 2009/0299334 A1    Dec. 3, 2009

Related U.S. Application Data

(60) Provisional application No. 60/730,899, filed on Oct. 27, 2005.

(51) Int. Cl.
*A61M 1/00* (2006.01)
(52) U.S. Cl. .................................. 604/544; 604/317
(58) Field of Classification Search .................. 604/172, 604/540, 544
See application file for complete search history.

(56) References Cited

U.S. PATENT DOCUMENTS
1,888,349 A    11/1932    Jacoby
(Continued)

FOREIGN PATENT DOCUMENTS
DE    10213411    10/2003
(Continued)

OTHER PUBLICATIONS
PCT/US2006/041633 filed Oct. 25, 2006 International Preliminary Report on Patentability dated Mar. 24, 2009.
(Continued)

*Primary Examiner* — Melanie Hand
(74) *Attorney, Agent, or Firm* — Rutan & Tucker, LLP (57) ABSTRACT

The present disclosure relates to a pre-wetted intermittent catheter apparatus including a collapsible container having a conduit positioned therein as well as a wetting fluid. The conduit has a lubricious coating disposed thereon such that the coating is hydrated upon contact with the wetting fluid in the container, providing a slippery surface for the conduit, which facilitates introduction of the conduit into a user. An introduction member may be incorporated into the distal end of the container and a disposal member may be incorporated into the proximal end, each respectively being positioned in an opening in the container and in communication with the conduit such that fluid flow through the conduit (positioned in the container) is enabled. A bag may be attached to or incorporated into the disposal member to provide a closed system such that the user or assistant is not exposed to potential contaminants. The collapsible container may be rigid or more flexible, but in either case, collapse of the container in use is easily accomplished by the user or assistant during introduction of the conduit into the user. Methods for inserting the catheter into a patient and draining urine from a patient are also disclosed.

28 Claims, 2 Drawing Sheets

U.S. PATENT DOCUMENTS

| | | |
|---|---|---|
| 2,912,981 A | 11/1959 | Keough |
| 2,919,697 A | 1/1960 | Kim |
| 3,556,294 A | 1/1971 | Walck et al. |
| 3,556,874 A | 1/1971 | McClain |
| 3,648,704 A | 3/1972 | Jackson |
| 3,695,921 A | 10/1972 | Shepard et al. |
| 3,699,964 A | 10/1972 | Ericson |
| 3,726,281 A | 4/1973 | Norton et al. |
| 3,794,042 A | 2/1974 | De Klotz et al. |
| 3,854,483 A | 12/1974 | Powers |
| 3,861,395 A | 1/1975 | Taniguchi |
| 3,898,993 A | 8/1975 | Taniguchi |
| 3,934,721 A | 1/1976 | Juster et al. |
| 3,967,728 A | 7/1976 | Gordon et al. |
| 4,026,296 A | 5/1977 | Stoy et al. |
| 4,055,682 A | 10/1977 | Merrill |
| 4,091,922 A | 5/1978 | Egler |
| 4,140,127 A | 2/1979 | Cianci et al. |
| 4,198,983 A | 4/1980 | Becker et al. |
| 4,230,115 A | 10/1980 | Walz, Jr. et al. |
| 4,245,639 A | 1/1981 | La Rosa |
| 4,246,909 A | 1/1981 | Wu et al. |
| 4,269,310 A | 5/1981 | Uson |
| 4,306,557 A | 12/1981 | North |
| 4,350,161 A | 9/1982 | Davis, Jr. |
| 4,366,901 A | 1/1983 | Short |
| 4,392,848 A | 7/1983 | Lucas et al. |
| 4,411,648 A | 10/1983 | Davis et al. |
| 4,515,593 A | 5/1985 | Norton |
| 4,517,971 A | 5/1985 | Sorbonne |
| 4,560,382 A | 12/1985 | Isono et al. |
| 4,571,241 A | 2/1986 | Christopher |
| 4,597,765 A | 7/1986 | Klatt |
| 4,610,670 A | 9/1986 | Spencer |
| 4,619,642 A | 10/1986 | Spencer |
| 4,681,572 A | 7/1987 | Tokarz et al. |
| 4,692,154 A | 9/1987 | Singery et al. |
| 4,696,672 A | 9/1987 | Mochizuki et al. |
| 4,704,102 A | 11/1987 | Guthery |
| 4,723,946 A | 2/1988 | Kay |
| 4,738,667 A | 4/1988 | Galloway |
| 4,754,877 A | 7/1988 | Johansson et al. |
| 4,759,753 A | 7/1988 | Schneider et al. |
| 4,762,128 A | 8/1988 | Rosenbluth |
| 4,773,901 A | 9/1988 | Norton |
| 4,784,651 A | 11/1988 | Hickey et al. |
| 4,811,847 A | 3/1989 | Reif et al. |
| 4,838,876 A | 6/1989 | Wong et al. |
| 4,886,508 A | 12/1989 | Washington |
| 4,888,005 A | 12/1989 | Dingeman et al. |
| 4,893,623 A | 1/1990 | Rosenbluth |
| 4,932,938 A | 6/1990 | Goldberg et al. |
| 4,957,487 A | 9/1990 | Gerow |
| 4,997,426 A | 3/1991 | Dingeman et al. |
| 5,007,897 A | 4/1991 | Kalb et al. |
| 5,045,078 A | 9/1991 | Asta |
| 5,087,252 A | 2/1992 | Denard |
| 5,098,379 A | 3/1992 | Conway et al. |
| 5,100,396 A | 3/1992 | Zamierowski |
| 5,137,671 A | 8/1992 | Conway et al. |
| 5,147,341 A | 9/1992 | Starke et al. |
| 5,174,290 A | 12/1992 | Fiddian-Green |
| 5,186,172 A | 2/1993 | Fiddian-Green |
| 5,188,596 A | 2/1993 | Condon et al. |
| 5,201,724 A | 4/1993 | Hukins et al. |
| 5,209,726 A | 5/1993 | Goosen |
| 5,209,728 A | 5/1993 | Kraus et al. |
| 5,224,953 A | 7/1993 | Morgentaler |
| 5,226,530 A | 7/1993 | Golden |
| 5,242,428 A | 9/1993 | Palestrant |
| 5,261,896 A | 11/1993 | Conway et al. |
| 5,269,755 A | 12/1993 | Bodicky |
| 5,269,770 A | 12/1993 | Conway et al. |
| 5,282,795 A | 2/1994 | Finney |
| 5,352,182 A | 10/1994 | Kalb et al. |
| 5,360,402 A | 11/1994 | Conway et al. |
| 5,370,899 A | 12/1994 | Conway et al. |
| 5,415,165 A | 5/1995 | Fiddian-Green |
| 5,417,666 A | 5/1995 | Coulter |
| 5,433,713 A | 7/1995 | Trotta |
| 5,445,626 A | 8/1995 | Gigante et al. |
| 5,454,798 A | 10/1995 | Kubalak et al. |
| 5,456,251 A | 10/1995 | Fiddian-Green |
| 5,466,229 A | 11/1995 | Elson et al. |
| 5,476,434 A | 12/1995 | Kalb et al. |
| 5,482,740 A | 1/1996 | Conway et al. |
| 5,501,669 A | 3/1996 | Conway et al. |
| 5,509,889 A | 4/1996 | Kalb et al. |
| 5,514,112 A | 5/1996 | Chu et al. |
| 5,520,636 A | 5/1996 | Korth et al. |
| 5,531,715 A | 7/1996 | Engelson et al. |
| 5,531,717 A | 7/1996 | Roberto et al. |
| 5,536,258 A | 7/1996 | Folden |
| 5,569,219 A | 10/1996 | Hakki et al. |
| 5,599,321 A | 2/1997 | Conway et al. |
| 5,601,537 A | 2/1997 | Frassica |
| 5,607,417 A | 3/1997 | Batich et al. |
| 5,616,126 A | 4/1997 | Malekmehr et al. |
| 5,624,395 A | 4/1997 | Mikhail et al. |
| 5,653,700 A | 8/1997 | Byrne et al. |
| 5,670,111 A | 9/1997 | Conway et al. |
| 5,688,516 A | 11/1997 | Raad et al. |
| 5,704,353 A | 1/1998 | Kalb et al. |
| 5,707,357 A | 1/1998 | Mikhail et al. |
| 5,711,841 A | 1/1998 | Jaker |
| 5,749,826 A | 5/1998 | Faulkner |
| 5,782,808 A | 7/1998 | Folden |
| 5,785,694 A | 7/1998 | Cohen et al. |
| 5,788,687 A | 8/1998 | Batich et al. |
| 5,800,339 A | 9/1998 | Salama |
| 5,817,067 A | 10/1998 | Tsukada et al. |
| 5,820,583 A | 10/1998 | Demopulos et al. |
| 5,853,518 A | 12/1998 | Utas et al. |
| 5,871,475 A | 2/1999 | Frassica |
| 5,895,374 A | 4/1999 | Rodsten et al. |
| 5,897,535 A | 4/1999 | Feliziani et al. |
| 5,941,856 A | 8/1999 | Kovacs et al. |
| 5,971,954 A | 10/1999 | Conway et al. |
| 5,980,483 A | 11/1999 | Dimitri et al. |
| 5,989,230 A | 11/1999 | Frassica |
| 6,004,305 A | 12/1999 | Hursman et al. |
| 6,024,751 A | 2/2000 | Lovato et al. |
| 6,050,934 A | 4/2000 | Mikhail et al. |
| 6,056,715 A | 5/2000 | Demopulos et al. |
| 6,059,107 A | 5/2000 | Nosted et al. |
| 6,063,063 A | 5/2000 | Harboe et al. |
| 6,090,075 A | 7/2000 | House |
| 6,156,049 A | 12/2000 | Lovato et al. |
| 6,162,201 A | 12/2000 | Cohen et al. |
| 6,183,461 B1 | 2/2001 | Matsuura et al. |
| 6,186,990 B1 | 2/2001 | Chen et al. |
| 6,190,353 B1 | 2/2001 | Makower et al. |
| 6,210,394 B1 | 4/2001 | Demopulos et al. |
| 6,221,056 B1 | 4/2001 | Silverman |
| 6,238,383 B1 | 5/2001 | Karram et al. |
| 6,254,570 B1 | 7/2001 | Rutner et al. |
| 6,254,585 B1 | 7/2001 | Demopulos et al. |
| 6,261,279 B1 | 7/2001 | Demopulos et al. |
| 6,293,923 B1 | 9/2001 | Yachia et al. |
| 6,299,598 B1 | 10/2001 | Bander |
| 6,306,422 B1 | 10/2001 | Batich et al. |
| 6,329,488 B1 | 12/2001 | Terry et al. |
| 6,340,359 B1 | 1/2002 | Silverman |
| 6,355,004 B1 | 3/2002 | Pedersen et al. |
| 6,358,229 B1 | 3/2002 | Tihon |
| 6,368,315 B1 | 4/2002 | Gillis et al. |
| 6,368,317 B2 | 4/2002 | Chang |
| 6,379,334 B1 | 4/2002 | Frassica |
| 6,383,434 B2 | 5/2002 | Conway et al. |
| 6,391,010 B1 | 5/2002 | Wilcox |
| 6,391,014 B1 | 5/2002 | Silverman |
| 6,398,718 B1 | 6/2002 | Yachia et al. |
| 6,402,726 B1 | 6/2002 | Genese |
| 6,409,717 B1 | 6/2002 | Israelsson et al. |
| 6,468,245 B2 | 10/2002 | Alexandersen et al. |
| 6,485,476 B1 | 11/2002 | von Dyck et al. |
| 6,544,240 B1 | 4/2003 | Borodulin et al. |

| Patent/Pub No. | Date | Name |
|---|---|---|
| 6,578,709 B1 | 6/2003 | Kavanagh et al. |
| 6,582,401 B1 | 6/2003 | Windheuser et al. |
| 6,602,244 B2 | 8/2003 | Kavanagh et al. |
| 6,613,342 B2 | 9/2003 | Aoki |
| 6,626,888 B1 | 9/2003 | Conway et al. |
| 6,629,969 B2 | 10/2003 | Chan et al. |
| 6,634,498 B2 | 10/2003 | Kayerod et al. |
| 6,648,906 B2 | 11/2003 | Lasheras et al. |
| 6,659,937 B2 | 12/2003 | Polsky et al. |
| 6,682,555 B2 | 1/2004 | Cioanta et al. |
| 6,695,831 B1 | 2/2004 | Tsukada et al. |
| 6,711,436 B1 | 3/2004 | Duhaylongsod |
| 6,716,895 B1 | 4/2004 | Terry |
| 6,719,709 B2 | 4/2004 | Whalen et al. |
| 6,730,113 B2 | 5/2004 | Eckhardt et al. |
| 6,736,805 B2 | 5/2004 | Israelsson et al. |
| 6,746,421 B2 | 6/2004 | Yachia et al. |
| 6,783,520 B1 | 8/2004 | Candray et al. |
| D496,266 S | 9/2004 | Nestenborg et al. |
| 6,824,532 B2 | 11/2004 | Gillis et al. |
| 6,835,183 B2 | 12/2004 | Lennox et al. |
| 6,840,379 B2 | 1/2005 | Franks-Farah et al. |
| 6,848,574 B1 | 2/2005 | Israelsson et al. |
| 6,849,070 B1 | 2/2005 | Hansen et al. |
| D503,335 S | 3/2005 | Risberg et al. |
| 6,869,416 B2 | 3/2005 | Windheuser et al. |
| 6,887,230 B2 | 5/2005 | Kubalak et al. |
| 6,918,924 B2 | 7/2005 | Lasheras et al. |
| 6,926,708 B1 | 8/2005 | Franks-Farah et al. |
| 6,939,339 B1 | 9/2005 | Axexandersen et al. |
| 6,941,171 B2 | 9/2005 | Mann et al. |
| 6,942,634 B2 | 9/2005 | Odland |
| 6,945,957 B2 | 9/2005 | Freyman |
| 6,949,598 B2 | 9/2005 | Terry |
| 7,001,370 B2 | 2/2006 | Kubalak et al. |
| 7,048,717 B1 | 5/2006 | Frassica |
| 7,059,330 B1 | 6/2006 | Makower et al. |
| 7,066,912 B2 | 6/2006 | Nestenborg et al. |
| 7,087,041 B2 | 8/2006 | von Dyck et al. |
| 7,087,048 B2 | 8/2006 | Israelsson et al. |
| 7,094,220 B2 | 8/2006 | Tanghoj et al. |
| 7,160,277 B2 | 1/2007 | Elson et al. |
| 7,166,092 B2 | 1/2007 | Elson et al. |
| 7,195,608 B2 | 3/2007 | Burnett |
| 7,244,242 B2 | 7/2007 | Freyman |
| 7,250,043 B2 | 7/2007 | Chan et al. |
| 7,255,687 B2 | 8/2007 | Huang et al. |
| 7,270,647 B2 | 9/2007 | Karpowicz et al. |
| 7,311,690 B2 | 12/2007 | Burnett |
| 7,311,698 B2 | 12/2007 | Tanghoj et al. |
| 7,380,658 B2 | 6/2008 | Murray et al. |
| 7,458,964 B2 | 12/2008 | Mosler et al. |
| 7,537,589 B2 | 5/2009 | Tsukada et al. |
| 2001/0031952 A1 | 10/2001 | Karram et al. |
| 2001/0047147 A1 | 11/2001 | Slepian et al. |
| 2001/0054562 A1 | 12/2001 | Pettersson et al. |
| 2002/0007175 A1 | 1/2002 | Chang |
| 2002/0045855 A1 | 4/2002 | Frassica |
| 2002/0055730 A1 | 5/2002 | Yachia et al. |
| 2002/0077611 A1 | 6/2002 | von Dyck et al. |
| 2002/0082551 A1 | 6/2002 | Yachia et al. |
| 2002/0087131 A1 | 7/2002 | Wolff et al. |
| 2002/0095133 A1 | 7/2002 | Gillis et al. |
| 2002/0099356 A1 | 7/2002 | Unger et al. |
| 2002/0103467 A1 | 8/2002 | Kubalak |
| 2002/0107467 A1 | 8/2002 | Levin |
| 2002/0156440 A1 | 10/2002 | Israelsson et al. |
| 2002/0165427 A1 | 11/2002 | Yachia et al. |
| 2003/0004496 A1 | 1/2003 | Tanghoj |
| 2003/0018293 A1 | 1/2003 | Tanghoj et al. |
| 2003/0018322 A1 | 1/2003 | Tanghoj et al. |
| 2003/0028174 A1 | 2/2003 | Chan et al. |
| 2003/0036802 A1 | 2/2003 | Lennox et al. |
| 2003/0055403 A1 | 3/2003 | Nestenborg et al. |
| 2003/0060807 A1 | 3/2003 | Tanghoj et al. |
| 2003/0065292 A1 | 4/2003 | Darouiche et al. |
| 2003/0130646 A1 | 7/2003 | Kubalak et al. |
| 2003/0135200 A1 | 7/2003 | Byrne |
| 2003/0163079 A1 | 8/2003 | Burnett |
| 2003/0195478 A1 | 10/2003 | Russo |
| 2003/0233084 A1 | 12/2003 | Slepian et al. |
| 2004/0030301 A1 | 2/2004 | Hunter |
| 2004/0034329 A1 | 2/2004 | Mankus et al. |
| 2004/0044307 A1 | 3/2004 | Richardson et al. |
| 2004/0049152 A1 | 3/2004 | Nayak |
| 2004/0049170 A1 | 3/2004 | Snell |
| 2004/0055925 A1 | 3/2004 | Franks-Farah et al. |
| 2004/0059280 A1 | 3/2004 | Makower et al. |
| 2004/0068251 A1 | 4/2004 | Chan et al. |
| 2004/0116551 A1 | 6/2004 | Terry |
| 2004/0127848 A1 | 7/2004 | Freyman |
| 2004/0133156 A1 | 7/2004 | Diaz et al. |
| 2004/0147871 A1 | 7/2004 | Burnett |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0176747 A1 | 9/2004 | Feneley |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0015076 A1 | 1/2005 | Giebmeyer et al. |
| 2005/0031872 A1 | 2/2005 | Schmidt et al. |
| 2005/0033222 A1 | 2/2005 | Haggstrom et al. |
| 2005/0043715 A1 | 2/2005 | Nestenborg et al. |
| 2005/0049577 A1 | 3/2005 | Snell et al. |
| 2005/0065499 A1 | 3/2005 | Douk et al. |
| 2005/0070882 A1 | 3/2005 | McBride |
| 2005/0080399 A1 | 4/2005 | Bolmsjo et al. |
| 2005/0096582 A1 | 5/2005 | Burnett |
| 2005/0101923 A1 | 5/2005 | Elson et al. |
| 2005/0101924 A1 | 5/2005 | Elson et al. |
| 2005/0107735 A1 | 5/2005 | Lennox et al. |
| 2005/0109648 A1 | 5/2005 | Kerzman et al. |
| 2005/0137522 A1 | 6/2005 | Aoki |
| 2005/0137582 A1 | 6/2005 | Kull-Osterlin et al. |
| 2005/0143690 A1 | 6/2005 | High |
| 2005/0148950 A1 | 7/2005 | Windheuser et al. |
| 2005/0197531 A1 | 9/2005 | Cabiri et al. |
| 2005/0199521 A1 | 9/2005 | Givens |
| 2005/0209580 A1 | 9/2005 | Freyman |
| 2005/0214443 A1 | 9/2005 | Madsen |
| 2005/0245901 A1 | 11/2005 | Floyd |
| 2005/0251108 A1 | 11/2005 | Frassica |
| 2005/0256447 A1 | 11/2005 | Richardson et al. |
| 2005/0273034 A1 | 12/2005 | Burnett |
| 2005/0283136 A1 | 12/2005 | Skarda |
| 2006/0025753 A1 | 2/2006 | Kubalak et al. |
| 2006/0030864 A1 | 2/2006 | Kennedy et al. |
| 2006/0036208 A1 | 2/2006 | Burnett |
| 2006/0041246 A1 | 2/2006 | Provost-tine et al. |
| 2006/0058777 A1 | 3/2006 | Nielsen |
| 2006/0064065 A1 | 3/2006 | Russo |
| 2006/0079835 A1 | 4/2006 | Frassica |
| 2006/0079854 A1 | 4/2006 | Kay et al. |
| 2006/0122566 A1 | 6/2006 | Huang et al. |
| 2006/0122568 A1 | 6/2006 | Elson et al. |
| 2006/0184112 A1 | 8/2006 | Horn et al. |
| 2006/0184145 A1 | 8/2006 | Ciok et al. |
| 2006/0196783 A1 | 9/2006 | Bruun et al. |
| 2006/0263404 A1 | 11/2006 | Nielsen et al. |
| 2006/0271019 A1 | 11/2006 | Stoller et al. |
| 2006/0276894 A1 | 12/2006 | Finley |
| 2006/0293642 A1 | 12/2006 | Israelsson et al. |
| 2007/0005041 A1 | 1/2007 | Frassica et al. |
| 2007/0010798 A1 | 1/2007 | Stoller et al. |
| 2007/0016169 A1 | 1/2007 | Utas et al. |
| 2007/0049879 A1 | 3/2007 | Gutierrez |
| 2007/0066963 A1 | 3/2007 | Tanghoj |
| 2007/0106233 A1 | 5/2007 | Huang et al. |
| 2007/0112327 A1 | 5/2007 | Yun et al. |
| 2007/0149929 A1 | 6/2007 | Utas et al. |
| 2007/0197957 A1 | 8/2007 | Hunter et al. |
| 2007/0225635 A1 | 9/2007 | Lynn |
| 2007/0225687 A1 | 9/2007 | House |
| 2007/0244449 A1 | 10/2007 | Najafi et al. |
| 2008/0015518 A1 | 1/2008 | Huang et al. |
| 2008/0021382 A1 | 1/2008 | Freyman |

| | | | | | |
|---|---|---|---|---|---|
| 2008/0027414 A1 | 1/2008 | Tanghoj et al. | EP | 1427467 | 6/2004 |
| 2008/0033471 A1 | 2/2008 | Paz et al. | EP | 1498151 | 1/2005 |
| 2008/0051762 A1 | 2/2008 | Tsukada et al. | EP | 1629860 | 3/2006 |
| 2008/0051763 A1 | 2/2008 | Frojd | EP | 1641510 | 4/2006 |
| 2008/0077099 A1 | 3/2008 | House | EP | 1642610 | 4/2006 |
| 2008/0082051 A1 | 4/2008 | Miller et al. | EP | 1642611 | 4/2006 |
| 2008/0091145 A1 | 4/2008 | House | FR | 2731345 | 9/1996 |
| 2008/0097362 A1 | 4/2008 | Mosler et al. | GB | 2284764 | 6/1995 |
| 2008/0097411 A1 | 4/2008 | House | GB | 2319507 | 5/1998 |
| 2008/0140010 A1 | 6/2008 | Kennedy et al. | WO | WO-8606284 | 11/1986 |
| 2008/0140052 A1 | 6/2008 | Moller et al. | WO | 9105577 A1 | 5/1991 |
| 2008/0171973 A1 | 7/2008 | House | WO | 9638192 A1 | 12/1996 |
| 2008/0171998 A1 | 7/2008 | House | WO | WO-9726937 | 7/1997 |
| 2008/0172016 A1 | 7/2008 | House | WO | WO-9741811 | 11/1997 |
| 2008/0179208 A1 | 7/2008 | Murray et al. | WO | WO-9806642 | 2/1998 |
| 2008/0200907 A1 | 8/2008 | Nestenborg | WO | WO-9811932 | 3/1998 |
| 2008/0243091 A1 | 10/2008 | Humphreys et al. | WO | WO-9819729 | 5/1998 |
| 2008/0249467 A1 | 10/2008 | Burnett et al. | WO | WO-9930761 | 6/1999 |
| 2008/0249482 A1 | 10/2008 | Erez | WO | WO-0016843 | 3/2000 |
| 2008/0275463 A1 | 11/2008 | High | WO | WO-0047494 | 8/2000 |
| 2009/0024111 A1 | 1/2009 | Borodulin et al. | WO | WO-0143807 | 6/2001 |
| 2009/0048537 A1 | 2/2009 | Lydon et al. | WO | WO-0152763 | 7/2001 |
| 2009/0137986 A1 | 5/2009 | Golden et al. | WO | WO-0193935 | 12/2001 |
| 2009/0149837 A1 | 6/2009 | Tanghoj et al. | WO | WO-0236192 | 5/2002 |
| | | | WO | WO-03002177 | 1/2003 |
| | | | WO | WO-03002178 | 1/2003 |

FOREIGN PATENT DOCUMENTS

| | | | | | |
|---|---|---|---|---|---|
| EP | 0217771 | 4/1987 | WO | WO-03008028 | 1/2003 |
| EP | 252918 | 1/1988 | WO | WO-03008029 | 1/2003 |
| EP | 479935 | 4/1992 | WO | 03064279 A1 | 8/2003 |
| EP | 677299 | 10/1995 | WO | WO-03092779 | 11/2003 |
| EP | 699086 | 3/1996 | WO | WO-2004030722 | 4/2004 |
| EP | 815037 | 1/1998 | WO | WO-2004045696 | 6/2004 |
| EP | 909249 | 4/1999 | WO | WO-2004050155 | 6/2004 |
| EP | 923398 | 6/1999 | WO | WO-2004052440 | 6/2004 |
| EP | 935478 | 8/1999 | WO | WO-2004056414 | 7/2004 |
| EP | 959930 | 12/1999 | WO | WO-2004075944 | 9/2004 |
| EP | 977610 | 2/2000 | WO | WO-2004089454 | 10/2004 |
| EP | 1023882 | 8/2000 | WO | WO-2005004964 | 1/2005 |
| EP | 1090656 | 4/2001 | WO | WO-2005061035 | 7/2005 |
| EP | 1115450 | 7/2001 | WO | WO 2005061035 A1 * | 7/2005 |
| EP | 1131022 | 9/2001 | WO | WO-2005092418 | 10/2005 |
| EP | 1145729 | 10/2001 | WO | WO-2007050685 | 5/2007 |
| EP | 1175355 | 1/2002 | | | |
| EP | 1237615 | 9/2002 | | | |
| EP | 1245205 | 10/2002 | | | |
| EP | 1308146 | 5/2003 | | | |
| EP | 1406690 | 4/2004 | | | |
| EP | 1409060 | 4/2004 | | | |
| EP | 1420846 | 5/2004 | | | |
| EP | 1420847 | 5/2004 | | | |

OTHER PUBLICATIONS

PCT/US2006/041633 filed Oct. 25, 2006 Search Report dated Aug. 12, 2008.

PCT/US2006/041633 filed Oct. 25, 2006 Written Opinion dated Aug. 12, 2008.

* cited by examiner

ENHANCED PRE-WETTED INTERMITTENT CATHETER WITH LUBRICIOUS COATING

PRIORITY

This application is a U.S. national stage application under 35 USC §371 of International Application No. PCT/US2006/041633, filed Oct. 25, 2006, claiming priority to U.S. Provisional Application No. 60/730,899, filed Oct. 27, 2005, each of which is incorporated by reference in its entirety into this application.

BACKGROUND OF THE INVENTION

Intermittent catheters are generally catheters or tubes having a rounded tip connected to a distal end that is inserted into the bladder of a patient or user, and a molded funnel connected to a distal end that remains outside the body of the patient or user. These types of catheters are typically utilized on a temporary basis to remove urine from the bladder of a patient or user. The distal tip may include slots or openings on the shaft to facilitate drainage of urine therefrom once the tip is positioned inside the bladder. Pre-wetted intermittent catheters are intermittent catheters having a highly lubricious coating on an outer surface thereof, which are packaged or otherwise brought into contact with fluid in order to provide a catheter with a slippery outer surface to facilitate insertion into the patient or user.

The current offerings of pre-wetted intermittent catheters can be broken up into three broad categories. In the first type, the catheter is packaged in a dry environment, but contains a lubricious coating that requires a wetting fluid in order to become hydrated. The wetting fluid is obtained from an external source by the user (e.g., sink, bottled water, etc.) and the catheter is positioned within the wetting fluid for a period of time to become hydrated. Use of this first type of intermittent catheter may prove difficult in the event that drainage must be performed by the user when no clean water or wetting fluid is available. Moreover, sterility of the catheter may be compromised due to the handling of the catheter by the user as wetting fluid is applied and thereafter during insertion.

A second type of pre-wetted intermittent catheter is also packaged in a dry environment and contains a lubricious coating. However, in this second type, the wetting fluid is positioned in a pouch or container within the catheter package itself such that to hydrate the catheter, the pouch or container must be opened when the user is ready for insertion. As with the first type, this second type may be disadvantageous due to the requirement that the catheter be exposed to the wetting fluid for a period of time to ensure hydration of the lubricious coating and also due to the likelihood that sterility of the catheter will be compromised during insertion.

A third type of pre-wetted intermittent catheter is packaged in a wet environment (i.e., the catheter is exposed to a wetting fluid within the catheter package). This third type overcomes the problems of having to wait for the catheter coating to hydrate, but has drawbacks in that the user may have difficulty handling the catheter due to its slippery surface and may contaminate the catheter prior to insertion due to the handling thereof.

Additionally, current intermittent catheters may drain urine into a bag. Following bladder drainage into the bag, the bag may need to be inverted and a tear is made across a notch. Urine is then drained into a receptacle from that tear. Such a process can be slow, messy, and subject to urine spills.

Thus, there is a need for a pre-wetted intermittent catheter that addresses needs of the patient or user, is easy to use, is quick, clean, capable of use with or without a bag, and is capable of maintaining sterility during insertion procedures.

BRIEF SUMMARY OF THE INVENTION

Accordingly, a pre-wetted intermittent catheter apparatus is described herein, the catheter apparatus in one embodiment including a collapsible container having a conduit positioned therein as well as a wetting fluid. The conduit has a lubricious coating disposed thereon such that the coating is hydrated upon contact with the wetting fluid in the container, providing a slippery surface for the conduit, which facilitates introduction of the conduit into a user. An introduction member may be incorporated into the distal end of the container and a disposal member may be incorporated into the proximal end, each respectively being positioned in an opening in the container and in communication with the conduit such that fluid flow through the conduit (positioned in the container) is enabled. A bag may be attached to or incorporated into the disposal member to provide a closed system such that the user or assistant is not exposed to potential contaminants. The collapsible container may be rigid or more flexible, but in either case, collapse of the container in use is easily accomplished by the user or assistant during introduction of the conduit into the user.

In one embodiment, a catheter apparatus includes a collapsible container having a proximal end and a distal end, a conduit positioned within the container, having a proximal end fixed to the container at the proximal end thereof and a distal end slidably positioned with respect to the container at the distal end thereof, wherein a coating is disposed on an outer surface on the conduit, and a wetting fluid disposed within the container.

One method of inserting a catheter into a patient includes removing a catheter apparatus from a package, the catheter apparatus comprising a collapsible container and a conduit positioned with the container, wherein a coating is disposed on an outer surface on the conduit and a wetting fluid is disposed within the container, removing a cap from a distal end of the container, inserting an introduction member into the patient, and pushing on a proximal end of the container in a direction toward the patient, wherein the container collapses upon itself and a portion of the conduit travels through the introduction member and into the patient.

One method of draining urine from a patient includes removing a catheter apparatus from a package, the catheter apparatus comprising a collapsible container and a conduit positioned with the container, wherein a coating is disposed on an outer surface on the conduit and a wetting fluid is disposed within the container, and wherein a disposal member is connected to a proximal end of the container, removing a cap from a distal end of the container, inserting an introduction member into the patient, and pushing on the proximal end of the container in a direction toward the patient, wherein the container collapses upon itself and a tip of the conduit travels through the introduction member and into the patient's bladder.

These and other embodiments, methods, features and advantages will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The catheter apparatus, as described herein, is discussed in the context of a urinary catheter for insertion into a user/patient bladder for drainage of urine therefrom. However, it should be appreciated that the catheter apparatus described could also be used for other applications not specifically mentioned herein, and therefore should not be limited to a urinary catheter application. Generally, the catheter apparatus includes a container and a conduit, such as a catheter or tube, positioned within the container. The conduit may have a round cross-sectional shape, an oval cross-sectional shape, or any other cross-sectional shape that may facilitate insertion into the body of a user/patient, and in particular into the bladder of the user/patient through the urethra. The conduit in accordance with various embodiments contains a lubricious and/or antimicrobial coating on at least an outer surface thereof. Suitable non-limiting examples of such coatings are disclosed in U.S. Pat. Nos. 6,329,488; 6,716,895; and 6,949,598; and U.S. Patent Application Publication No. US 2004/0116551, each of which is incorporated by reference into this application as if fully set forth herein.

As used herein, the reference terms "proximal" and "distal" (proximal being closer than distal) refer to the proximity with respect to a health care professional or person other than a patient that is assisting the patient in utilizing the catheter apparatus, or in the case that a user is implementing the catheter apparatus without the aid of another, refer to the proximity with respect to a point external to the user's body. Thus, for example, a region or section of the catheter apparatus that is close to a health care professional or the user's hand when the catheter apparatus is being utilized is referred to as "proximal," while a region or section of the catheter apparatus distanced from a health care professional or the user's hand when the catheter apparatus is being utilized is referred to as "distal."

According to one embodiment, the container is configured to collapse upon itself to facilitate introduction of the conduit by a user and to prevent direct contact by the user with the conduit. The container may include an introduction member at the distal end thereof to facilitate introduction of the conduit and/or a disposal member at the proximal end thereof to facilitate disposal of the drained urine. According to various embodiments, the container is made of a gas impermeable material and contains within it a wetting fluid. The purpose of the wetting fluid is to maintain hydration of the lubricious coating such that upon insertion of the conduit into a user, at least an outer portion thereof is extremely slippery, facilitating insertion.

Figure 1:
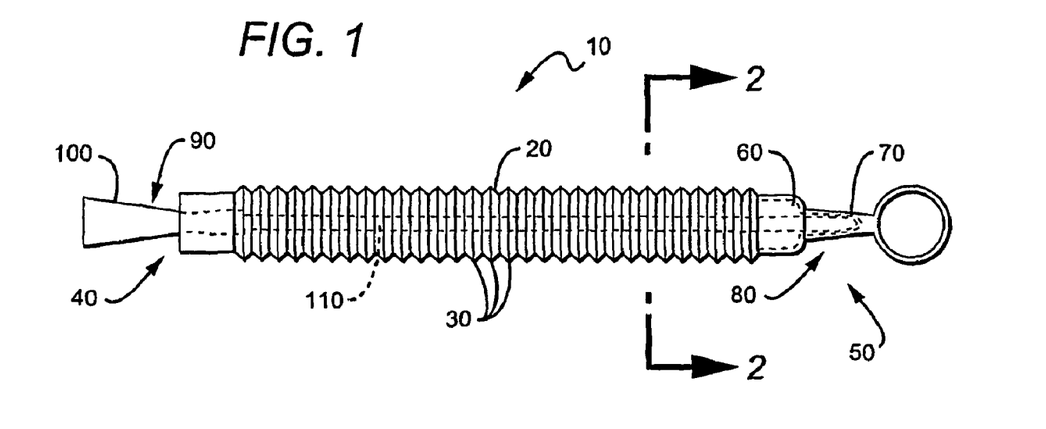
FIG. 1 is a side view of one embodiment of a catheter apparatus in an initial rest position prior to use.
Figure 2:
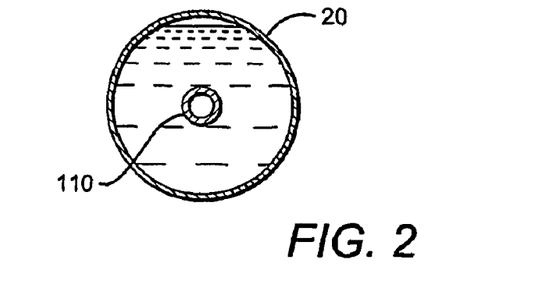
FIG. 2 is a cross-section of the catheter apparatus of FIG. 1.
Figure 3:
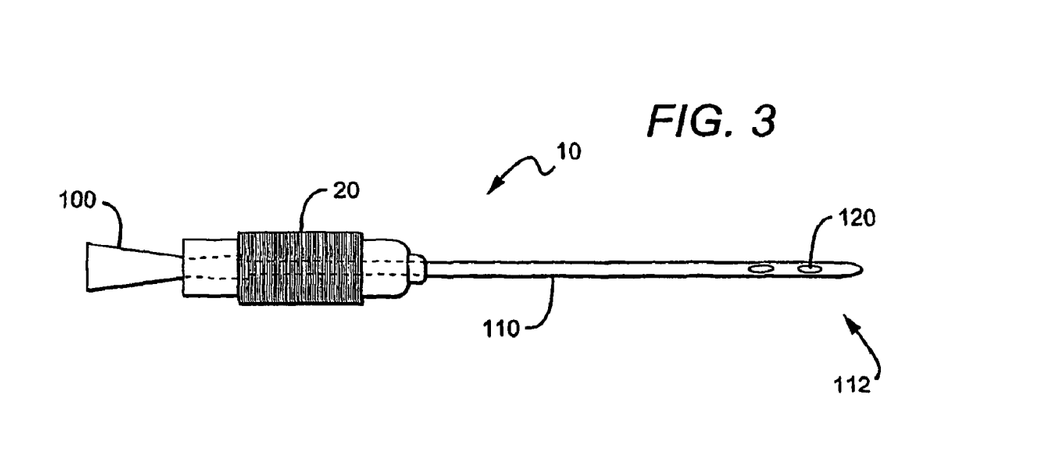
FIG. 3 is a side view of the catheter apparatus of FIG. 1 in a deployed position.

Referring now to FIGS. 1-3, one embodiment of a pre-wetted intermittent catheter apparatus 10 is shown. The catheter apparatus in this embodiment includes a container 20 made of a gas impermeable material, the container having a tubular outer surface with a plurality of pleats or folds 30 along a middle portion thereof between a proximal end section 40 and a distal end section 50. Suitable gas impermeable materials for the container 20 include, for example, polymers, such as polypropylene and polyethylene. The pleats or folds 30 in the outer surface of the container 20 permit the container to compress or collapse upon itself in accordion-like fashion. According to another embodiment, the container 20 does not contain pleats or folds 30 but instead is comprised of a collapsible material such as, for example, a foil material or the like, or films, such as polymeric films (e.g., polypropylene films, polyethylene films, etc.). Both the proximal and distal end sections 40, 50 of the container 20 include an opening. The container shown in FIG. 1 is generally rigid, meaning that it will generally maintain its shape in a rest state.

Connected to the distal end section 50 of the container 20, in this embodiment, is an introduction member 60. In the embodiment shown in FIG. 1, the introduction member 60 is disposed partially within the container 20 and partially outside of the container, such that an introducer tip 70 extends through the opening in the distal end section 50 of the container 20. A base portion of the introduction member 60 is positioned within the container 20 and can be attached to an inner surface of the container by any suitable method known to one skilled in the art. In another embodiment, the introduction member 60 is integral to the container 20. In the case that the introduction member 60 is a separate component attached to the container 20, it may be made of a material, such as, for example, a polymeric material (e.g., polyethylene, polypropylene, etc.). In the embodiment shown, a cap 80 is placed over the distal end section 50 of the container 20. The cap 80 can be secured to the distal end section 50 by friction fit, threaded engagement (i.e., either the cap or the distal end section contains threads, protrusions, etc. while the other contains grooves, detents, recesses, etc. to receive the threads, protrusions, etc.), or other like securing methods known to one skilled in the art.

Connected to the proximal end section 40 of the container 20 is a disposal member 90. In the embodiment shown in FIG. 1, the disposal member 90 is disposed partially within the container 20 and partially outside of the container, such that a drainage funnel 100 extends through the opening in the proximal end section 40 of the container 20. A distal portion of the disposal member 90 is positioned within the container 20 and, in one embodiment, is sealingly attached to a proximal end of a conduit 110, such that fluid communication is established therewith, as well as to an inner surface of the container. In another embodiment the disposal member 90 is attached only to the conduit 110 in sealing fashion and is friction fit through the opening in the proximal end section 40 of the container 20. In still another embodiment, the disposal member 90 is integral to the container 20. In one embodiment, the drainage funnel 100 of the disposal member 90 is configured such that it can be inserted into, or otherwise connected to, a bag (see, for example, FIG. 5) and sealed thereto such that fluid communication between the disposal member 90 and the bag is established and a closed system is provided to prevent exposure to contaminants to the user or assistant (nurse, family member, etc.). Drainage of a user's bladder can then take place directly into the bag, which can subsequently be detached from the disposal member 90 and either emptied and sanitized, or disposed of, in the case that the bag is made of a disposable material. In one embodiment the bag includes an extension member extending from an opening therein that both sealingly connects to the disposal member 90 of the container and is shaped to receive the cap 80, initially positioned over the distal end section 50 of the container 20.

Positioned within the container 20 is a conduit (e.g., tube, catheter, etc.) 110 that is fixedly attached at its proximal end to the disposal member 90, being in fluid communication therewith. The connection between the conduit 110 and the disposal member 90 can be accomplished by any method known to bond such materials together, for example by molding and/or chemically bonding (with, e.g., cyclohexanone). In the embodiment shown in FIG. 1, the distal end of the conduit 110 is slidably positioned within the introduction member 60 (shown in FIG. 1 to be initially within the introducer tip 70), such that upon collapse of the container 20, the conduit, having a fixed proximal end and a sliding distal end, will extend from the distal end 50 of the container. A sliding seal member is incorporated into the introduction member 60 or container 20, through which the conduit 110 is slidably positioned, to permit sliding of the conduit with respect to the container while preventing loss or leakage of the wetting fluid from the container. Due to the positioning and action of the conduit 110 with respect to the collapsible container 20, extension of the distal end of the conduit 110 from the distal opening in the container is related to the length of the container in an inverse fashion, such that as the length of the container gets smaller due to compression or collapse thereof, the distal end of the conduit is spaced a greater distance from the distal opening of the container. This is illustrated in FIG. 3, showing the catheter apparatus 10 in a deployed position, in which the conduit 110 has been extended by pushing the proximal end of the catheter apparatus 10 in a distal direction (i.e., away from the user) to collapse the container onto itself.

Different lengths, sizes (e.g., diameter, width, etc.), and configurations are possible for the conduit 10, depending on the user's anatomy. For example, in one embodiment for an adult male human, the length of the conduit 110 may be in the range of about 8 to about 18 cm and have an elliptical cross-sectional shape similar to the shape of the male urethra. In the embodiment shown in FIGS. 1-3, the conduit 110 has a circular cross-sectional shape. The distal end of the conduit 110 includes a tip 112 in the embodiment of FIG. 3, the tip having a rounded atraumatic shape (e.g., bullet shape, etc.) and a plurality of openings 120 or "eyes" in the sides of the tip that connect with a central conduit lumen such that placement of the conduit tip into a urine pool in the bladder results in drainage of urine therefrom. As mentioned above, at least a portion of the outer surface of the conduit 110 is coated with a lubricious coating, which when contacted by a wetting fluid, becomes hydrated. The hydration of the lubricious coating results in a surface with a low coefficient of friction such that the conduit 110 is easily slidable into the body of a user. The lubricious coating can be any coating capable of providing a lubricious property, such as those described in U.S. Pat. No. 6,329,488.

Figure 4:
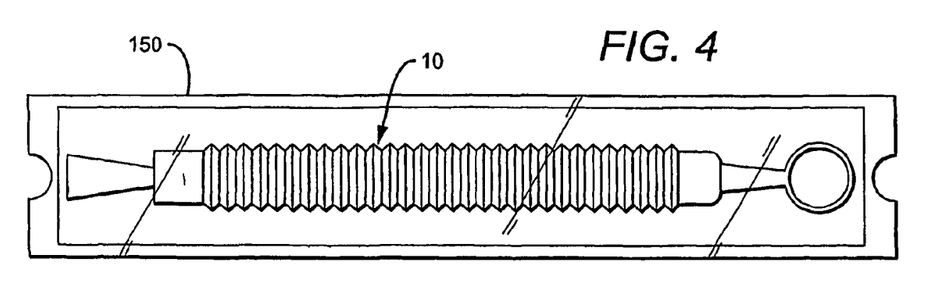
FIG. 4 is the catheter apparatus of FIG. 1, shown packaged in one embodiment of a package.
Figure 5:
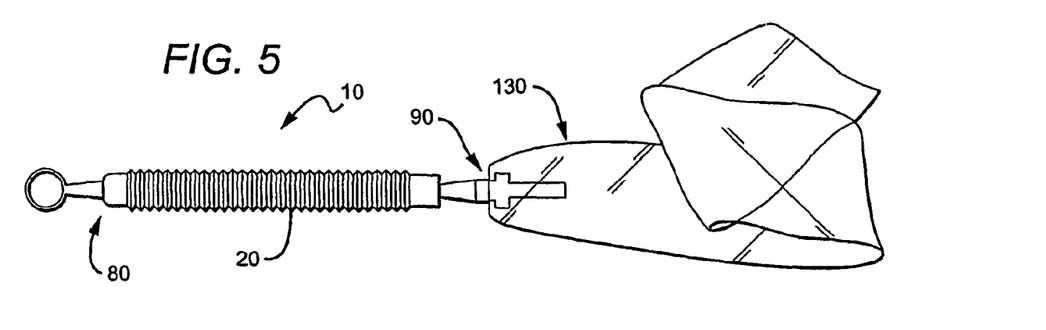
FIG. 5 is the catheter apparatus of FIG. 1 with an attached disposable bag.
Figure 6:
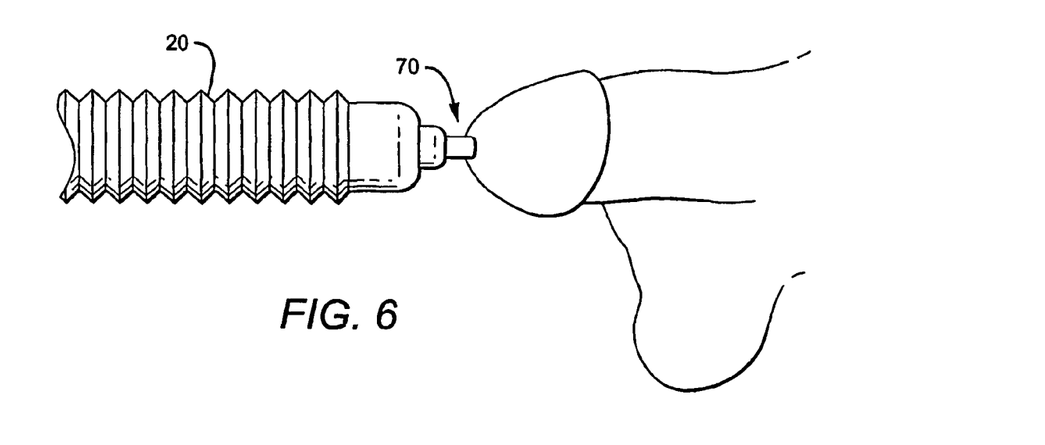
FIG. 6 is the catheter apparatus of FIG. 1, shown in a partially deployed position into a model.

Referring now to the device as illustrated in FIGS. 1-6, the packaged catheter apparatus 10 as shown in FIG. 4 is removed from the package 150. The conduit 110, being contained completely within the container 20 and surrounded by wetting fluid, is in a sterile condition and remains that way due to the cap 80. The bag 130, which may be separately packaged or packaged along with the catheter apparatus 10, is connected to the disposal member 90 extending from the proximal end section 40 of the catheter apparatus 10 as shown in FIG. 5 (in alternate embodiments not employing a bag, such as the one shown in FIG. 4, this step is not performed). Once the bag 130 has been connected to the catheter apparatus 10 and the user is ready for insertion, the cap 80 is removed from the distal end 50 of the container 20 and the introducer tip 70 is placed into the user, as shown in FIG. 6. The user or assistant then holds the catheter apparatus 10 at a proximal end (e.g., the user grasps the disposal member 90 with one hand) and pushes in a distal direction to extend the conduit 110 into the user and eventually into the user's bladder, while simultaneously collapsing the container 20 onto itself. This action minimizes or eliminates exposure of the conduit 110 to conditions or contaminants outside of the container.

According to another embodiment, the catheter apparatus is coiled or folded into a package to provide as compact of an article as reasonably possible for shipping and storing. The package can be in the form of a flexible article, such as package 150, that includes a transparent plastic cover sealed to a backing, or a semi-rigid article, such as a box or carton (e.g., made of cardboard, plastic, etc.).

Drainage of urine from the user's bladder then takes place and following evacuation, the proximal end of the catheter apparatus is pulled in a proximal direction (i.e., toward the user), while the introducer tip 70 is held in place. This action results in the conduit 110 returning fully inside the container 20 so that the user or assistant is not exposed to potential contaminants. In the embodiment in which a bag 130 is attached to the proximal end section 40 of the catheter apparatus 10, the bag 130 is subsequently removed and disposed of (or emptied and sanitized). In an embodiment in which a bag 130 is not attached to the proximal end section 40 of the catheter apparatus 10, the disposal member 90 is directed into a disposal collection member or waste disposal apparatus, such as a toilet, during evacuation of the bladder.

The collapsible container embodiment illustrated in FIGS. 1-6 provides a number of advantages, such as, for example, a storage area for the wetting fluid, a sterile barrier for the conduit during insertion and a secure handing area during insertion. The design is well suited for low dexterity users, specifically for use utilizing only one hand, since a very low force is necessary to advance the conduit and collapse the container.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A catheter apparatus, comprising:
    a collapsible container having a proximal end and a distal end, wherein the container comprises an introduction member connected to the container distal end, the introduction member including a tip that extends through an opening in the container distal end;
    a conduit positioned within the container, having a proximal end fixed to the container at the proximal end thereof and a distal end slidably positioned with respect to the container at the distal end thereof, wherein a coating is disposed on an outer surface on the conduit; and
    a wetting fluid disposed within the container.

2. The catheter apparatus according to claim 1, wherein the container proximal end is connected to a disposal member, and wherein a lumen of the conduit is in fluid communication with the disposal member.

3. The catheter apparatus according to claim 1, wherein the conduit distal end includes an atraumatic tip that is aligned with the opening in the container distal end.

4. The catheter apparatus according to claim 1, wherein the conduit distal end is positioned within the introduction member.

5. The catheter apparatus according to claim 1, wherein the collapsible container comprises a generally tubular outer surface with a plurality of pleats.

6. The catheter apparatus according to claim 1, wherein the collapsible container comprises a gas impermeable material.

7. The catheter apparatus according to claim 1, further comprising a removable cap configured to attach to the container distal end, the cap including a removal feature.

8. The catheter apparatus according to claim 1, further comprising a disposal member including a funnel portion extending from the container proximal end.

9. The catheter apparatus according to claim 1, further comprising a disposal member including a distal portion positioned within the container, the conduit proximal end being in sealing connection with the disposal member distal portion.

10. The catheter apparatus according to claim 1, further comprising a disposal member including a disposable bag.

11. The catheter apparatus according to claim 10, wherein said disposable bag comprises a drain port for draining the contents of said bag.

12. A packaged catheter apparatus, comprising the catheter apparatus according to claim 1 and a sterile package.

13. The packaged catheter apparatus according to claim 12, further comprising a disposable bag.

14. The packaged catheter apparatus according to claim 12, wherein the sterile package comprises a gas permeable material, at least a portion of the gas permeable material being transparent.

15. A method of inserting a catheter into a patient, comprising:
    removing a catheter apparatus from a package, the catheter apparatus comprising a collapsible container and a conduit positioned within the container, wherein a coating is disposed on an outer surface on the conduit and a wetting fluid is disposed within the container;
    removing a cap from a distal end of the container; inserting an introduction member into the patient; and
    pushing on a proximal end of the container in a direction toward the patient, wherein the container collapses upon itself and a portion of the conduit travels through the introduction member and into the patient.

16. The method according to claim 15, wherein the collapsible container comprises a generally tubular outer surface with a plurality of pleats, wherein adjacent pleats come into contact with one another when the proximal end of the container is pushed in a direction toward the patient.

17. A method of draining urine from a patient, comprising:
    removing a catheter apparatus from a package, the catheter apparatus comprising a collapsible container and a conduit positioned with the container, wherein a coating is disposed on an outer surface on the conduit and a wetting fluid is disposed within the container, and wherein a disposal member is connected to a proximal end of the container;
    removing a cap from a distal end of the container; inserting an introduction member into the patient; and
    pushing on the proximal end of the container in a direction toward the patient, wherein the container collapses upon itself and a tip of the conduit travels through the introduction member and into the patient's bladder.

18. The method according to claim 17, wherein the disposal member comprises a funnel extending from the proximal end of the container, further comprising directing the funnel into a disposal collection member.

19. The method according to claim 17, wherein the disposal member comprises a disposable bag, further comprising removing the bag from the container following drainage of the patient's bladder and placing the cap over an opening in the bag.

20. The method according to claim 17, wherein the disposal member comprises a disposable bag having a drain port at the proximal end thereof, further comprising draining the bag into a receptacle by opening said drain port.

21. A catheter apparatus, comprising:
    a collapsible container having a proximal end and a distal end, wherein the container proximal end is connected to a disposal member;
    a conduit positioned within the container, having a proximal end fixed to the container at the proximal end thereof and a distal end slidably positioned with respect to the container at the distal end thereof, wherein a coating is disposed on an outer surface on the conduit, and wherein a lumen of the conduit is in fluid communication with the disposal member; and
    a wetting fluid disposed within the container.

22. A catheter apparatus, comprising:
    a collapsible container having a proximal end and a distal end;
    a conduit positioned within the container, having a proximal end fixed to the container at the proximal end thereof and a distal end slidably positioned with respect to the container at the distal end thereof, wherein a coating is disposed on an outer surface on the conduit;
    a wetting fluid disposed within the container; and
    a removable cap configured to attach to the container distal end, the cap including a removal feature.

23. A catheter apparatus, comprising:
    a collapsible container having a proximal end and a distal end;
    a conduit positioned within the container, having a proximal end fixed to the container at the proximal end thereof and a distal end slidably positioned with respect to the container at the distal end thereof, wherein a coating is disposed on an outer surface on the conduit;
    a wetting fluid disposed within the container; and
    a disposal member including a funnel portion extending from the container proximal end.

24. A catheter apparatus, comprising:
a collapsible container having a proximal end and a distal end;
a conduit positioned within the container, having a proximal end fixed to the container at the proximal end thereof and a distal end slidably positioned with respect to the container at the distal end thereof, wherein a coating is disposed on an outer surface on the conduit;
a wetting fluid disposed within the container; and
a disposal member including a distal portion positioned within the container, the conduit proximal end being in sealing connection with the disposal member distal portion.

25. A catheter apparatus, comprising:
a collapsible container having a proximal end and a distal end;
a conduit positioned within the container, having a proximal end fixed to the container at the proximal end thereof and a distal end slidably positioned with respect to the container at the distal end thereof, wherein a coating is disposed on an outer surface on the conduit;
a wetting fluid disposed within the container; and
a disposal member including a disposable bag.

26. The catheter apparatus according to claim 25, wherein the disposable bag comprises a drain port for draining the contents thereof.

27. A packaged catheter apparatus, comprising:
a catheter apparatus, comprising:
   a collapsible container having a proximal end and a distal end;
   a conduit positioned within the container, having a proximal end fixed to the container at the proximal end thereof and a distal end slidably positioned with respect to the container at the distal end thereof, wherein a coating is disposed on an outer surface on the conduit; and
   a wetting fluid disposed within the container;
a sterile package; and
a disposable bag.

28. The packaged catheter apparatus according to claim 27, wherein the sterile package comprises a gas permeable material, at least a portion of the gas permeable material being transparent.

* * * * *